(12) United States Patent
Dietrich et al.

(10) Patent No.: US 9,994,491 B2
(45) Date of Patent: Jun. 12, 2018

(54) COMPOSITION OF A MAGNESIUM SULPHATE-UREA COMPOUND

(71) Applicant: K+S Aktiengesellschaft, Kassel (DE)

(72) Inventors: Armin Dietrich, Weissenborn (DE); Guido Baucke, Schenklengsfeld (DE); Stefan Thenert, Heringen (DE); Ulrich Kleine-Kleffmann, Bad Hersfeld (DE); Wolfgang Walczyk, Heringen (DE); Stefan Dressel, Kassel (DE); Ludger Waldmann, Telgte (DE)

(73) Assignee: K+S AKTIENGESELLSCHAFT, Kassel (DE)

( * ) Notice: Subject to any disclaimer, the term of this patent is extended or adjusted under 35 U.S.C. 154(b) by 271 days.

(21) Appl. No.: 14/653,668

(22) PCT Filed: Dec. 20, 2013

(86) PCT No.: PCT/EP2013/077724
§ 371 (c)(1),
(2) Date: Oct. 14, 2015

(87) PCT Pub. No.: WO2014/096372
PCT Pub. Date: Jun. 26, 2014

(65) Prior Publication Data
US 2016/0046534 A1 Feb. 18, 2016

(30) Foreign Application Priority Data
Dec. 21, 2012 (DE) .................. 10 2012 025 141

(51) Int. Cl.
*C05C 9/00* (2006.01)
*C05D 9/00* (2006.01)
(Continued)

(52) U.S. Cl.
CPC ............... *C05C 9/00* (2013.01); *A01G 1/001* (2013.01); *A01G 22/00* (2018.02); *A01G 25/00* (2013.01);
(Continued)

(58) Field of Classification Search
CPC ............. C05C 9/00; C05D 9/00; C07C 273/02
See application file for complete search history.

(56) References Cited

U.S. PATENT DOCUMENTS 9,663,410 B2 * 5/2017 Kleine-Kleffmann .... C05C 9/00

FOREIGN PATENT DOCUMENTS

| WO | 2013/098367 | * 7/2013 |
| WO | 2013 098367 | 7/2013 |

OTHER PUBLICATIONS

Colin W. Whittaker et al, "Magnesium sulfate-cobalt sulfate-urea-water system at 30 C", Journal of American Chemical Society, vol. 58, Oct. 1, 1936, XP-002678412, 1975-1977.*

(Continued)

*Primary Examiner* — Wayne Langel
(74) *Attorney, Agent, or Firm* — Grüneberg and Myers PLLC (57) ABSTRACT

The present invention relates to compositions containing at least 80% by weight, especially at least 90% by weight, based on the total weight of the composition, of at least one magnesium sulfate-urea compound selected from the compound of the formula (I) and mixtures of the compound of the formula (I) with the compound of the formula (II): [MgSO$_4$.mCO(NH$_2$)$_2$.nH$_2$O] (I), [MgSO$_4$.xCO(NH$_2$)$_2$.yH$_2$O] (II), in which m and x are each in the range from 0.9 to 1.1, n is in the range from 1.9 to 2.1 and y is in the range from 2.9 to 3.1, where the compositions, based on the total weight of the composition, contain less than 10% by weight of free MgSO$_4$ in the form of the anhydrate or in the (Continued)

| MgSO$_4$ • CO(NH$_2$)$_2$ • 2 H$_2$O | | MgSO$_4$ • CO(NH$_2$)$_2$ • 3 H$_2$O | |
|---|---|---|---|
| d (Å) | rel. Intensity (%) | d (Å) | rel. intensity (%) |
| 9.637 | 5 | 10.166 | 100 |
| 6.937 | 100 | 6.139 | 6 |
| 4.940 | 19 | 5.223 | 3 |
| 4.917 | 17 | 5.093 | 7 |
| 4.611 | 3 | 4.806 | 7 |
| 4.180 | 6 | 4.252 | 11 |
| 3.469 | 23 | 4.076 | 18 |
| 3.384 | 25 | 3.896 | 4 |
| 3.349 | 45 | 3.853 | 33 |
| 3.287 | 11 | 3.604 | 3 |
| 3.257 | 28 | 3.518 | 6 |
| 3.157 | 43 | 3.399 | 51 |
| 2.900 | 5 | 3.202 | 7 |
| 2.621 | 8 | 3.007 | 10 |
| 2.605 | 12 | 2.957 | 5 |
| 2.567 | 5 | 2.932 | 12 |
| 2.540 | 3 | 2.756 | 14 |
| 2.473 | 6 | 2.707 | 3 |
| 2.434 | 4 | 2.551 | 4 |
| 2.314 | 6 | 2.492 | 8 |
| 2.100 | 7 | 2.294 | 5 |
| 2.031 | 4 | 2.265 | 4 |
| 1.955 | 4 | 2.261 | 7 |
| 1.736 | 3 | 2.139 | 5 |
| | | 2.129 | 4 | form of hydrates of magnesium sulfate and less than 10% by weight of unbound urea. The invention also relates to the production of the compositions and to the use thereof as fertilizers or fertilizer additive.

16 Claims, 4 Drawing Sheets

(51) Int. Cl.
*C07C 273/02* (2006.01)
*C05D 5/00* (2006.01)
*C05D 9/02* (2006.01)
*C05G 3/08* (2006.01)
*A01G 1/00* (2006.01)
*A01G 25/00* (2006.01)

(52) U.S. Cl.
CPC ............. *C05D 5/00* (2013.01); *C05D 9/00* (2013.01); *C05D 9/02* (2013.01); *C05G 3/08* (2013.01); *C07C 273/02* (2013.01); *Y02P 60/218* (2015.11)

(56) References Cited

OTHER PUBLICATIONS

Sulaimankulov, K. et al, "Reactions of urea with sulfates of bivalent metal. I. The isotherms of the system water-urea-magnesium sulfate at 0, 30, and 45", Zhurnal Neorganicheskoi Khimii (1957), 2, 2668-75.*
International Search Report dated Jul. 3, 2014 in PCT/EP2013/077724 Filed Dec. 20, 2013.

* cited by examiner

Figure 1:

| MgSO$_4$ • CO(NH$_2$)$_2$ • 2 H$_2$O | | MgSO$_4$ • CO(NH$_2$)$_2$ • 3 H$_2$O | |
|---|---|---|---|
| d (Å) | rel. intensity (%) | d (Å) | rel. intensity (%) |
| 9.637 | 5 | 10.166 | 100 |
| 6.937 | 100 | 6.139 | 6 |
| 4.940 | 19 | 5.223 | 3 |
| 4.917 | 17 | 5.093 | 7 |
| 4.611 | 3 | 4.806 | 7 |
| 4.180 | 6 | 4.252 | 11 |
| 3.469 | 23 | 4.076 | 18 |
| 3.364 | 25 | 3.896 | 4 |
| 3.349 | 45 | 3.853 | 33 |
| 3.287 | 11 | 3.604 | 3 |
| 3.257 | 28 | 3.518 | 6 |
| 3.157 | 43 | 3.399 | 51 |
| 2.900 | 5 | 3.202 | 7 |
| 2.621 | 8 | 3.007 | 10 |
| 2.605 | 12 | 2.957 | 5 |
| 2.567 | 5 | 2.932 | 12 |
| 2.540 | 3 | 2.756 | 14 |
| 2.473 | 6 | 2.707 | 3 |
| 2.434 | 4 | 2.551 | 4 |
| 2.314 | 6 | 2.492 | 6 |
| 2.100 | 7 | 2.294 | 5 |
| 2.031 | 4 | 2.265 | 4 |
| 1.955 | 4 | 2.261 | 7 |
| 1.736 | 3 | 2.139 | 5 |
| | | 2.129 | 4 |

Figure 2: TGA

Figure 3: TGA

Figure 4: FTIR spectrum of the compound of formula (I)

Figure 5: FTIR spectrum of the compound of formula (II)

COMPOSITION OF A MAGNESIUM SULPHATE-UREA COMPOUND

This application is National Stage Entry of PCT/EP2013/077724, filed Dec. 20, 2013, and claims priority to German application 10 2012 025 141.6, filed Dec. 21, 2012.

The present invention relates to compositions of a magnesium sulfate-urea compound of formula (I) and of mixtures of the compound of formula (I) with the compound of formula (II):

$$[MgSO_4 \cdot mCO(NH_2)_2 \cdot nH_2O] \quad (I),$$

$$[MgSO_4 \cdot xCO(NH_2)_2 \cdot yH_2O] \quad (II),$$

wherein m and x lie in the range from 0.9 to 1.1, n in the range from 1.9 to 2.1 and y in the range from 2.9 to 3.1, to the production of the compositions and to the use thereof as fertilizers or fertilizer additive.

Although magnesium is the eighth-most abundant element and constitutes approximately 1.94% of the earth's crust, soils often exhibit a magnesium deficiency. Therefore magnesium salts are widely used as fertilizers or fertilizer additives. In particular, salts of magnesium are used as fertilizers or fertilizer additives. Usually these salts are used as magnesium sulfate in conjunction with macronutrients such as potassium, phosphorus or nitrogen as well as with trace elements such as manganese, zinc, copper, iron, cobalt, molybdenum or boron.

In principle, it of interest to provide as many macronutrients and micronutrients as possible together in a fertilizer composition. However, the use of magnesium and nitrogen together is subject to limits. For example, a simple solid mixture of Epsom salts ($MgSO_4 \cdot 7 H_2O$) and urea is not stable during storage. Even after a short time, the two components of the mixture react to form pasty masses, which because of their highly hygroscopic nature also deliquesce readily and therefore are difficult to handle, and in particular cannot be incorporated in solid fertilizer compositions.

Magnesium sulfate-urea compositions are known mainly from the literature. For example, Y. Yee et al., *Journal of the American Chemical Society*, 1937, 59, 5701, describe the production of magnesium sulfate-urea complexes, wherein the ratio of magnesium sulfate to urea is 1 to 6 or 1 to 5 ($MgSO_4 \cdot 6CO(NH_2)_2 \cdot 2H_2O$, $MgSO_4 \cdot 5CO(NH_2)_2 \cdot 2H_2O$). To produce these compounds, Epsom salts ($MgSO_4 \cdot 7H_2O$) are mixed with urea in an alcoholic solution. The aforesaid products then precipitate out, depending on the stoichiometric ratio of Epsom salts to urea.

C. W. Whittaker et al. *Journal of American Society*, 1936, 58, 1975 describe investigations on the phase diagram of magnesium sulfate-urea-water at 30° C. A compound of the formula $MgSO_4 \cdot CO(NH_2)_2 \cdot 3H_2O$ is postulated as one of the phases. Equimolar amounts of Epsom salts ($MgSO_4 \cdot 7H_2O$) are mixed with urea to produce this compound. Under these conditions, a crystalline product precipitates out. Our own investigations revealed that this is a mixture of the compound of the formula $MgSO_4 \cdot CO(NH_2)_2 \cdot 3H_2O$ with Epsom salts ($MgSO_4 \cdot 7H_2O$) and unbound urea and not the pure substance $MgSO_4 \cdot CO(NH_2)_2 \cdot 3H_2O$. It is not possible to extract the compound $MgSO_4 \cdot CO(NH_2)_2 \cdot 3H_2O$ from this mixture, since the compound decomposes during purification attempts.

T. Todorov et al. *Acta Crystallographica, Section C: Crystal Structure Communications*, 1998, 54(12), 1758 report on further magnesium sulfate-urea complexes, wherein the ratio of magnesium sulfate to urea is 1 to 6 ($MgSO_4 \cdot 6CO(NH_2)_2 \cdot 0.5H_2O$). This complex is produced by evaporating an aqueous solution consisting of corresponding molar concentrations of Epsom salts and urea.

Z. Fengxing et al. *Journal of Inorganic Chemistry*, 1997, 13(4), 375 report on solubility and stability investigations of a quaternary system $K_2SO_4$—$MgSO_4$—$CO(NH_2)_2$—$H_2O$. In this case a ternary phase of the composition $MgSO_4 \cdot CO(NH_2)_2 \cdot 2H_2O$ was allegedly identified. However, the reported experimental data of the magnesium-urea complex $MgSO_4 \cdot CO(NH_2)_2 \cdot 2H_2O$ are contradictory and not plausible. The inventors' own investigations have shown that, for example, the diffraction diagram presented therein is not the same as the diffraction diagram of the substance identified as $MgSO_4 \cdot CO(NH_2)_2 \cdot 2H_2O$.

W. Xiaolan et al. *Acta Physico-Chemica Sinica*, 1998, 14(3), 237 report on isothermal phase diagrams of a quaternary system $KCl(K_2SO_4)$—$MgCl_2 (MgSO_4)$—$CO(NH_2)_2$—$H_2O$. Therein it is mentioned in Table 2 that $MgSO_4 \cdot CO(NH_2)_2 \cdot 2H_2O$ besides other complexes was identified as a component of the precipitate. However, the investigations described therein are contradictory, since the solution and solid compositions indicated in this respect do not even contain any sulfate. Not the least because of the lack of spectroscopic data, the results described therein cannot be regarded as credible. The isolation of $MgSO_4 \cdot CO(NH_2)_2 \cdot 2H_2O$ is not described.

Swiss Patent CH 364277 describes a process for production of magnesium-containing urea prill with low biuret content. For this purpose 6-9 wt % magnesium sulfate relative to the starting anhydrous urea is dissolved in an aqueous urea solution and then the solution is evaporated in a thin-film evaporator at pressures of >200 torr and a temperature of >130° C. The melt obtained is then sprayed to obtain prills. The resulting magnesium-sulfate containing prills have a moisture content of 0.6-0.8 wt %. The relatively good storage stability of the prills can presumably be attributed to the fact that these prills on the one hand are almost anhydrous and on the other hand have a very low magnesium sulfate content.

WO 2013/098367 describes the composition and production of a magnesium-urea compound of formula (II) as well as the use thereof as fertilizer or fertilizer additive. Mixtures of various magnesium-urea compounds are not mentioned.

The object of the invention is therefore to provide a composition of magnesium sulfate-urea that can be produced systematically, simply, selectively and without interfering secondary products as well as quantitatively.

Surprisingly it was found that, by means of suitable processes, it is possible in rapid and simple manner to produce the magnesium sulfate-urea compound of formula (I) as well as mixtures of the compound of formula (I) with the compound of formula (II) in very good yields as pure, crystalline and storage-stable compositions, which do not suffer from the disadvantages of the prior art and which in particular are only slightly hygroscopic and also do not tend to deliquesce. The compositions obtained in this way can therefore be incorporated particularly well in fertilizer compositions.

The subject matter of the invention are therefore compositions that contain at least 80 wt %, especially at least 90 wt %, relative to the total weight of the composition, of at least one magnesium sulfate-urea compound selected from the compound of formula (I) and mixtures of the compound of formula (I) with the compound of formula (II):

$$[MgSO_4 \cdot mCO(NH_2)_2 \cdot nH_2O] \quad (I),$$

$$[MgSO_4 \cdot xCO(NH_2)_2 \cdot yH_2O] \quad (II),$$

wherein m and x lie in the range from 0.9 to 1.1, n in the range from 1.9 to 2.1 and y in the range from 2.9 to 3.1, wherein the compositions, relative to the total weight of the composition, contain less than 10 wt %, in particular less than 5 wt % of free MgSO$_4$ in anhydrous form or in the form of hydrates of magnesium sulfate, and less than 10 wt %, in particular less than 5 wt % of unbound urea. In particular, m in formula (I) has the value 1. In particular, n in formula (I) has the value 2. In particular, x in formula (II) has the value 1. In particular, y in formula (II) has the value 3.

The inventive compositions are solid, usually crystalline compositions that are not or only slightly hygroscopic compositions and that also do not deliquesce. In contrast to the compositions of the compound of formula (I) and of mixtures of the compound of formula (I) with the compound of formula (II) known from the prior art, they have only a small proportion or no detectable contents of starting substances. In addition, the compound of formula I alone as well as mixtures of the compound of formula (I) with the compound of formula (II) are accessible in very good yields and with high selectivity as well as obtainable in storage-stable, slightly hygroscopic form. Moreover, these compositions can be easily produced in powder form or in the form of granules and therefore can be used in simple manner as fertilizers or introduced into conventional fertilizer compositions. Furthermore, by dissolving the compositions in a solvent, such as water, it is possible to produce solutions of the compositions. Furthermore, the inventive compositions usually have only very low or no detectable contents of biuret. As a rule, the proportion of biuret is at most 1.2 wt %, especially at most 0.5 wt % relative to the total weight of the composition.

According to the invention, the inventive compositions contain less than 10 wt %, especially less than 5 wt %, relative to the total weight of the composition, of unbound urea and at the same time less than 10 wt %, relative to the total weight of the composition, of free MgSO$_4$ in anhydrous form or in the form of urea-free hydrates of magnesium sulfate. Preferably the composition contains less than 5 wt % of free MgSO$_4$ in anhydrous form or in the form of urea-free hydrates of magnesium sulfate or less than 5 wt % of unbound urea, in each case relative to the total weight of the composition. In particular, the composition contains less than 5 wt %, especially less than 3 wt % of free MgSO$_4$ in anhydrous form or in the form of urea-free hydrates of magnesium sulfate and at the same time less than 5 wt %, especially less than 3 wt % of unbound urea, in each case relative to the total weight of the composition.

The proportion of free MgSO$_4$ in anhydrous form or in the form of hydrates of magnesium sulfate, such as Epsom salts, magnesium sulfate monohydrate or magnesium sulfate hexahydrate as well as the proportion of free urea can be determined by means of x-ray powder diffraction by comparing a powder diffraction diagram with reference powder diffraction diagrams of the impurities such as MgSO$_4$ in anhydrous form or in the form of Epsom salts or else magnesium sulfate hexahydrate and urea. Such methods are known to the person skilled in the art and may be performed in well known ways, for example using powder x-ray diffraction software: "EVA" ver. 12.0.0.0 of the Bruker AXS Co., database: Powder Diffraction Files (PDF-2, Release 1999; Data Sets 1-49, plus 70-86) of the International Centre for Diffraction Data (ICDD).

From the absence of reflections characteristic of impurities, it may additionally be concluded that the proportion of the respective impurity is vanishingly small according to qualitative evaluation of the RDA diagram. The characteristic reflections for MgSO$_4$ in anhydrous form or in the form of Epsom salts or magnesium sulfate hexahydrate as well as urea can be found in the literature or in pertinent databases such as those of the International Centre for Diffraction Data (JCPDS). In an x-ray powder diffraction diagram (Cu—Kα radiation: λ=1.5413 Å) recorded at 25° C., the compound of formula (I) contained in the inventive compositions exhibits at least 3 and in particular at least 5 and especially at least 7 or all d-values of the following Table 1, wherein it preferably exhibits at least 3, in particular at least 5 and especially at least 7 of those reflections having a relative intensity greater than 8% relative to the intensity of the strongest peak (100% relative intensity). Table 1 presents the characteristic reflections of compound (I) as lattice spacings d (in Ångström), which can be calculated from the 2θ values of Bragg's Law.

TABLE 1

| Compound of formula (I) | |
|---|---|
| d-value (Å) | rel. intensity (%) |
| 6.937 | 100 |
| 3.349 | 45 |
| 3.157 | 43 |
| 3.257 | 28 |
| 3.364 | 25 |
| 3.469 | 23 |
| 4.940 | 19 |
| 4.917 | 17 |
| 2.605 | 12 |
| 3.287 | 11 |
| 2.621 | 8 |
| 2.100 | 7 |
| 2.314 | 6 |
| 2.473 | 6 |
| 4.180 | 6 |
| 2.900 | 5 |
| 2.567 | 5 |
| 9.637 | 5 |
| 2.434 | 4 |
| 2.031 | 4 |
| 1.955 | 4 |
| 4.611 | 3 |
| 2.540 | 3 |
| 1.736 | 3 |

Figure 1:
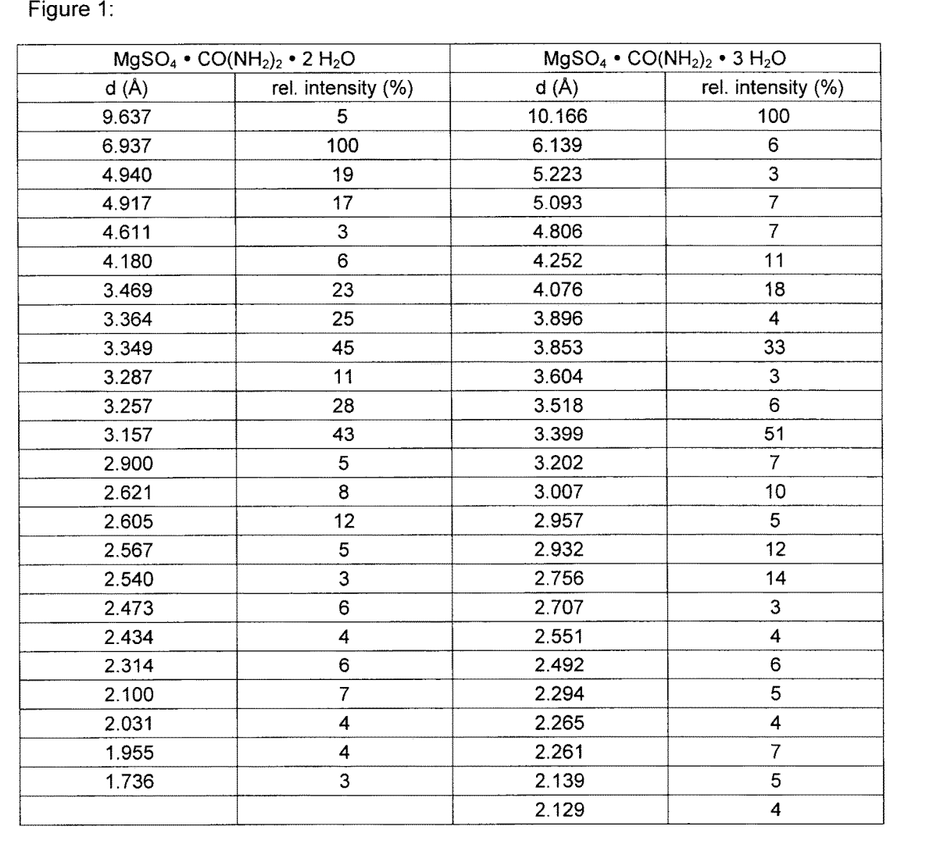
FIG. 1: List of the characteristic reflections (expressed as d-values in Ångström, determined at 298 K using Cu—Kα radiation: α=1.5413 Å) and their relative intensity in the x-ray powder diagram of the compound of formula (I) ($MgSO_4 \cdot CO(NH_2)_2 \cdot 2H_2O$) and of the compound of formula (II) ($MgSO_4 \cdot CO(NH_2)_2 \cdot 3H_2O$). Values: d in Ångström (1 Å=0.1 nm), relative reflection intensity is reported relative to the 100% reflection (≥3%).

On the basis of the reflections listed in the following Table 2, the compounds contained in the inventive compositions can be identified in an x-ray powder diffraction diagram (Cu—Kα radiation: λ=1.5413 Å) of the composition recorded at 25° C., wherein typically at least 3 and in particular at least 5 of the indicated d-values with a relative intensity greater than 10% are used for identification. A complete listing of the d-values is presented in FIG. 1.

TABLE 2

| Impurity | d-value (Å) | rel. intensity (%) |
|---|---|---|
| Urea | 3.9916 | 100 |
|  | 3.6138 | 24 |
|  | 3.0435 | 25 |
| MgSO$_4$•7 H$_2$O | 4.2160 | 100 |
|  | 4.2000 | 75 |
|  | 5.3400 | 30 |
|  | 5.9800 | 30 |
| MgSO$_4$•H$_2$O | 3.4050 | 100 |
|  | 4.8150 | 75 |
|  | 3.3510 | 70 |
|  | 3.3130 | 70 |
| MgSO$_4$ | 3.5300 | 100 |
|  | 3.6100 | 70 |
|  | 4.1500 | 30 |

The stoichiometry of the compound can be determined by elemental analysis in which the impurities present are taken into consideration.

A first preferred embodiment of the invention relates to compositions with a high proportion of the compound of formula (I), in particular compositions in which the proportion of the compound of formula (I) relative to the total content of compounds of formulas (I) and (II) is at least 90 wt %, in particular at least 95 wt % and especially such compositions that do not contain any detectable contents of the compound of formula (II).

A second preferred embodiment of the invention relates to compositions that contain a mixture of the compound of formula (I) and the compound of formula (II), in particular compositions in which the proportion of the compound of formula (I) relative to the total content of compounds of formulas (I) and (II) lies in the range of 20 to 90 wt %, in particular in the range of 30 to 85 wt %.

Furthermore, a process for production of the inventive compositions of the magnesium sulfate-urea compound of formula (I) and mixtures of the compound of formula (I) with the compound of formula (II) has been found, which process is characterized in that anhydrous magnesium sulfate is reacted with urea and water. This process is referred to hereinafter as process 1. Process 1 permits the production in particular of inventive compositions with a high proportion of the compound of formula (I), in particular the production of compositions in which the proportion of the compound of formula (I) relative to the total content of compounds of formulas (I) and (II) is at least 90 wt %, in particular at least 95 wt % and especially such compositions that do not contain any detectable contents of the compound of formula (II). By variation of the reaction conditions as explained hereinafter, process 1 also permits the production of compositions that contain a mixture of the compound of formula (I) and the compound of formula (II).

Preferably anhydrous magnesium sulfate in the form of a powder is used, wherein at least 90 wt %, in particular at least 95 wt % of the particles have a particle diameter smaller than 200 µm, in particular a maximum of 100 µm. Such powders can be obtained by grinding commercial, anhydrous magnesium sulfate. Preferably urea is used in the form of granules, wherein at least 90 wt %, in particular at least 95 wt % of the particles have a particle diameter smaller than 1 mm. Such powders or granules can be obtained by grinding commercial, pilled urea. The particle diameter of the powder particles of magnesium sulfate as well as the particle diameter of the urea powder or granules can be determined by sieve analysis. The use of commercial, prilled urea usually leads to compositions with high proportions of compound of formula (II).

According to the invention, anhydrous magnesium sulfate, urea and water reacted in process 1 in the for the compound in a mole ratio of magnesium sulfate to urea in the range of 1:0.9 to 1:1.1, in particular 1:0.95 to 1:1.05 and especially 1:0.98 to 1:1.02 and a ratio of magnesium sulfate to water in the range of 1:2.0 to 1:4.0, in particular 1:2.95 to 1:3.5 and especially 1:2.98 to 1:3.02.

In particular, for the reaction according to process 1, anhydrous magnesium sulfate will be mixed with urea in the aforesaid mole ratio and water will be added thereto in the aforesaid mole ratio. A possible embodiment of process 1 is described in Example 1.

The reaction according to process 1 takes place at temperatures above 75° C. In particular, the reaction will be carried out at temperatures in the range of 80 to 95° C. In this connection, preferably a temperature of 95° C. will not be exceeded. Temperatures above 95° C. may lead to undesired formation of biuret. Preferably the usually liquid or plastic reaction mixture will be continuously mixed during the reaction, for example by means of suitable stirring or kneading apparatuses or by means of extruders. Typically the initially liquid or plastic reaction mixture solidifies with advancing reaction time.

After the reaction of the starting substances, these are usually allowed to cool to room temperature. It has proved advantageous, immediately after the reaction of the starting substances or after cooling, to allow the obtained composition to mature for a certain time at a temperature in the range of 15 to 40° C., in particular 20 to 30° C., before it is further processed. The maturation time will usually be in the range from 15 minutes to 20 hours, preferably in the range of 2 to 12 hours, in particular in the range of 3 to 8 hours.

Furthermore, it has proved especially advantageous to carry out the reaction in a mixing apparatus having at least one rotating mixing implement, for example a kneader or intensive mixer (e.g. an Eirich mixer). In this way, by increasing the speed of the mixing implement, size reduction and/or granulation of the reaction mixture and adjustment of the desired grain sizes or particle diameters can already be achieved during or directly after the reaction. For this purpose, the speed of the mixer will be increased within a few minutes after the beginning of the setting process (manifested by the development of a pasty mass). After the reaction has ended (approximately 3 to 30 minutes) and the mixer has been emptied, the product continues to mature—for example as described hereinabove.

According to a preferred embodiment of process 1, the solid composition obtained after the maturation process is subjected to size reduction. Standard apparatuses for size reduction of solids may be used for size reduction of the composition, advantageously beater or impact mills, including also jaw-type crushers, rotary crushers, roller crushers, hammer crushers, thumb-type crushers, screw-type crushers, roller mills, impact mills and chip crushers. Usually size reduction will be continued until at least 90 wt % of the particles have a diameter smaller than 5 mm. Preferably size reduction will be carried out such that at least 90 wt % of the particles have a particle diameter in the range of 0.1 to 5 mm. The particle diameter can be determined by sieve analysis.

A further advantage of process 1 consists in the possibility, by using a suitable mixing apparatus, for example a kneader or intensive mixer, e.g. an Eirich mixer, to accomplish size reduction and/or granulation of the reaction mixture and thus adjustment of the aforesaid grain sizes or particle diameters already during the reaction in a mixing apparatus having at least one rotating mixing implement, by increasing the speed of the mixing implements. In this case the maturation of the compound of formula (I) advantageously takes place relatively rapidly (within hours).

The inventive process 1, as well as process 2 to be described hereinafter, makes it possible to produce the compound of formula (I) and mixtures of the compound of formula (I) with the compound of formula (II) in high yields, usually up to at least 90% in practice, in particular at least 95 to 100% relative to magnesium sulfate and urea. The proportion of free magnesium sulfate in the obtained composition, whether in anhydrous form or in the form of a urea-free hydrate, is less than 10 wt %, frequently less than 5 wt %, in particular less than 3 wt %. Furthermore, the inventive process makes it possible to produce compositions of the compound of formula (I) that contain less than 10 wt %, frequently less than 5 wt % and in particular less than 3 wt % of unbound urea. The compositions produced in this way contain, if at all, only a very small proportion of biuret, usually at most 1.2 wt %, in particular at most 0.5 wt % relative to the total weight of the composition.

In contrast to the process of the prior art, the inventive processes 1 and 2 do not require any additional solvent or filtration and drying steps and can therefore be carried out particularly simply and with high energy efficiency.

Besides process 1 described in the foregoing, a process 2 for production of the inventive compositions of magnesium sulfate-urea compounds of formula (I) and mixtures of the compound of formula (I) with the compound of formula (II) has also been found, which process is characterized in that a composition containing at least 80 wt %, in particular at least 90 wt %, relative to the total weight of the composition, of the magnesium sulfate-urea compound of formula (II) and less than 10 wt %, in particular less than 5 wt % and especially less than 3 wt % of free $MgSO_4$ in anhydrous form or in the form of hydrates of magnesium sulfate and less than 10 wt %, in particular less than 5 wt % and especially less than 3 wt % of unbound urea is dried at temperatures in the range of 60 to 95° C., in particular at temperatures in the range of 65 to 85° C. This process is referred to hereinafter as process 2. A possible embodiment of process 2 is described in Example 2.

Process 2 permits the production not only of inventive compositions with a high proportion of the compound of formula (I), in particular the production of compositions in which the compound of formula (I), relative to the total content of compounds of formulas (I) and (II), is at least 90 wt %, in particular at least 95 wt %, and especially of such compositions that do not contain any detectable contents of the compound of formula (II), but also of compositions that contain a mixture of the compound of formula (I) and the compound of formula (II). The proportion of compound (I) can be controlled simply by the duration of the reaction.

For the production of the inventive compositions according to process 2, a magnesium sulfate-urea compound of formula (II)

$$[MgSO_4 \cdot xCO(NH_2)_2 \cdot yH_2O] \qquad (II),$$

wherein x lies in the range from 0.9 to 1.1 and y lies in the range from 2.9 to 3.1 is preferably used in the form of a composition which, relative to its total weight, less than 10 wt %, in particular less than 5 wt % and especially less than 3 wt % of free $MgSo_4$ in anhydrous form or in the form of hydrates of magnesium sulfate and/or less than 10 wt %, in particular less than 5 wt % and especially less than 3 wt % of unbound urea. In particular, x in formula (II) has the value 1. In particular, y in formula (II) has the value 3.

In an x-ray powder diffraction diagram (Cu—Kα radiation: λ=1.5413 Å) recorded at 25° C., the compound of formula (II) contained in the compositions exhibits at least 3 and in particular at least 5 and especially at least 7 or all d-values of the following Table 3, wherein it preferably exhibits at least 3, in particular at least 5 and especially at least 7 of those reflections having a relative intensity greater than 8% relative to the intensity of the strongest peak (100% relative intensity). Table 3 presents the characteristic reflections of compound (II) as lattice spacings d (in Ångström), which can be calculated from the 2θ values of Bragg's Law.

TABLE 3

| d-value (Å) | rel. intensity (%) |
|---|---|
| 10.1656 | 100 |
| 3.3994 | 63 |
| 3.8527 | 39 |
| 4.0752 | 21 |
| 2.9318 | 15 |
| 2.7558 | 15 |

TABLE 3-continued

| d-value (Å) | rel. intensity (%) |
|---|---|
| 4.2520 | 13 |
| 3.0064 | 13 |
| 4.8050 | 9 |
| 3.2015 | 9 |
| 5.0928 | 8 |
| 2.2609 | 8 |
| 2.4920 | 8 |
| 6.1384 | 7 |
| 3.5177 | 7 |
| 2.5505 | 7 |
| 2.2649 | 6 |
| 2.9572 | 6 |
| 2.2944 | 6 |
| 2.1393 | 6 |
| 2.1293 | 6 |
| 2.4767 | 5 |

Preferably, in process 2, a composition of the compound of formula (II) is used in the form of a powder or granules, wherein at least 90 wt % of the particles have a particle diameter smaller than 5 mm. The particle diameter can be determined by sieve analysis.

The production of compositions of the compound of formula (II) is described in WO 2013/098367.

Compositions of the compound of formula (II) can be produced by the reaction of anhydrous magnesium sulfate, urea and water in the stoichiometry necessary for the compound. The reaction is usually carried out at temperatures below 70° C., preferably at temperatures of at most 60° C., in particular at temperatures in the range of 30 to 60° C. For production of compositions of the compounds of formula (II), usually magnesium sulfate, urea and water are reacted with one another in the stoichiometry necessary for the compound, i.e. in a mole ratio of magnesium sulfate to urea in the range of 1:0.9 to 1:1.1, in particular 1:0.95 to 1:1.05 and especially 1:0.98 to 1:1.02 and a ratio of magnesium sulfate to water in the range of 1:2.9 to 1:3.1, in particular 1:2.95 to 1:3.05 and especially 1:2.98 to 1:3.02.

This reaction of anhydrous magnesium sulfate, urea and water for the production of compositions of the compound of formula (II) is exothermic. Thus it has proved advantageous to carry out the reaction of the reaction partners anhydrous magnesium sulfate, urea and water by utilizing the heats of reaction. Preferably a temperature of 70° C., in particular 60° C. will not be exceeded in this case. If necessary, the reaction mixture will be cooled. In particular, the reaction is carried out at temperatures in the range of 30 to 60° C. If necessary, provisions will be made to return water that evaporates during the reaction back to the reaction. Preferably the usually liquid or plastic reaction mixture will be continuously mixed during the reaction, for example by means of suitable stirring or kneading apparatuses or by means of extruders. After the end of the reaction, the resulting composition is usually allowed to cool to ambient temperature. Typically this yields a solid mass, which can be subjected to size reduction in well known ways.

A further possibility for production of compositions of the compound of formula (II) consists in first reacting a mixture of Epsom salts ($MgSO_4 \cdot 7H_2O$) with urea in the mole ratio of Epsom salts to urea in the range of 1:0.9 to 1:1.1, in particular 1:0.95 to 1:1.05 and especially 1:0.98 to 1:1.02 then adding further urea to the resulting mixture in the course of the reaction. Preferably, in the course of the reaction for production of the compounds of formula (II), further urea in a content of 10 to 30 mol % relative to the initially used content of urea is added to the mixture of Epsom salts ($MgSO_4 \cdot 7H_2O$) and urea. The addition may be carried out in one portion or in several portions or else continuously. The addition of the further urea is usually carried out at a time at which Epsom salts ($MgSO_4 \cdot 7H_2O$) and urea have already been mixed with one another. Preferably reaction is carried out at temperatures in the range of 20 to 70° C. and in particular in the range of 40 to 60° C. Since the reaction exhibits hardly any evolution of heat, the mixture of Epsom salts and urea will be heated if necessary to the desired temperature. Preferably the usually liquid or plastic reaction mixture will be continuously mixed during the reaction, for example by means of suitable stirring or kneading apparatuses. In this way a reaction mixture in the form of an aqueous suspension is obtained. From this the compound of formula (II) or the composition containing it can be isolated by standard methods for separating solid and liquid phases, for example by filtering or centrifuging. Usually a drying step will then be carried out. Preferably drying will be carried out at temperatures in the range of 30 to 70° C. and in particular in the range of 30 to 50° C. The compounds of formula (II) produced in this way typically precipitate in finely divided form.

A further possibility for production of compositions of the compound of formula (II) consists in first reacting a mixture of anhydrous magnesium sulfate, urea and Epsom salts ($MgSO_4 \cdot 7H_2O$). In this procedure, preferably anhydrous magnesium sulfate, urea and Epsom salts are reacted in the stoichiometry necessary for the compound, i.e. in a mole ratio of anhydrous magnesium sulfate to urea in the range of 1:1.65 to 1:1.85 and the mole ratio of magnesium sulfate to Epsom salts in the range of 1:0.65 to 1:0.85, wherein the mole ratio of urea to the total content of anhydrous magnesium sulfate and Epsom salts lies in the range of 0.9:1 to 1.1:1. Preferably the mixture of the foregoing starting substances is first heated to 30 to 60° C., in particular 40 to 55° C. Preferably the usually liquid or plastic reaction mixture will be continuously mixed during the reaction, for example by means of suitable stirring or kneading apparatuses or by means of extruders. The resulting pasty mass of the obtained composition solidifies upon cooling to ambient temperature. This typically yields a solid mass, which can be subjected to size reduction in well known ways.

Preferably, in process 2, the composition of the magnesium sulfate-urea compound of formula (II), obtainable according to one of the processes described hereinabove, will be dried for 10 to 30 hours, in particular 15 to 28 hours at temperatures in the range of 65 to 95° C., in particular in the range of 65 to 85° C. Usually temperatures above 95° C. will not be used, since they may lead to undesired formation of biuret. It is possible to take samples during drying, in order to establish the end point of complete reaction by gravimetric tests or x-ray analyses.

It is possible to mix the composition of the compound of formula (II) continuously during heating, for example by means of suitable stirring or kneading apparatuses.

The inventive composition of the compound of formula (I) and mixtures of the compound of formula (I) with the compound of formula (II) obtainable according to process 2 typically precipitates in finely divided form, wherein less than 90 wt % of the particles have a particle diameter larger than 5 mm. Preferably at least 90 wt % of the particles have a particle diameter smaller than 2 mm, particularly preferably smaller than 1 mm. The particle diameter can be determined by sieve analysis.

The inventive process 2 also makes it possible to produce the compound of formula (I) alone or else mixtures of the compound of formula (I) with the compound of formula (II) in high yield, usually at least 70%, in particular at least 80%, especially at least 90% relative to magnesium sulfate. The proportion of free magnesium sulfate, whether in anhydrous form or in the form of a urea-free hydrate, in the composition obtained in this way is less than 10 wt % and in particular less than 5 wt % and especially less than 3 wt % relative to the total weight of the composition. The proportion of free urea in the composition obtained in this way is less than 10 wt % and in particular less than 5 wt % and especially less than 3 wt % relative to the total weight of the composition. The compositions produced in this way contain, if at all, only a very small proportion of biuret, usually at most 1.2 wt %, in particular at most 0.5 wt % relative to the total weight of the composition.

The invention further relates to the use of the inventive compositions as fertilizers or as fertilizer additive.

The inventive compositions are suitable as such as fertilizers and in themselves they represent a nitrogen-magnesium-sulfur fertilizer. However, they are also suitable in particular as the nitrogen supplier for conventional magnesium-sulfur fertilizer compositions. Thus nitrogen-magnesium-sulfur fertilizer compositions can be prepared simply by addition to conventional magnesium-sulfur fertilizer compositions.

Such nitrogen-magnesium-sulfur fertilizer compositions contain the compound of formula (I) or mixtures of the compound of formula (I) with the compound of formula (II), wherein the total content of compound (I) and compound (II) typically in a proportion of 1 to 100%.

Besides the compound of formula (I) or the mixtures of the compound of formula (I) with the compound of formula (II) and if necessary magnesium sulfate, preferably in the form of Epsom salts, the nitrogen-magnesium-sulfur fertilizer compositions may contain further macronutrients such as phosphorus, preferably in the form of phosphates, and/or potassium, as well as micronutrients such as manganese, zinc, copper, iron, cobalt, molybdenum and/or boron if necessary. In this case, manganese and zinc are preferably used in the form of their sulfates. Copper, cobalt and iron are preferably used in the form of chelates, for example with EDTA. Boron is preferably used as sodium borate or boric acid. Molybdenum is preferably used as sodium or ammonium molybdate or as a mixture thereof.

Preferably the inventive compositions are used as additives in fertilizers containing Epsom salts. Such fertilizers or fertilizer compositions are novel and also subject matter of the invention. In particular, the inventive fertilizer composition contains not only Epsom salts but also 1 to 90 wt %, in particular 5 to 50 wt % and especially 10 to 30 wt %, relative to the total weight of the fertilizer composition, of the compound of formula (I) and the compound of formula (II), as well as one or more of the aforesaid micronutrients if necessary. The proportion of the micronutrients, calculated as the element, will usually be no higher than 30 wt % relative to the total weight of the fertilizer composition, and it frequently lies, if desired, in the range of 0.1 to 10 wt %.

The inventive compositions of the compound of formula (I) or of the mixtures of the compound of formula (I) with the compound of formula (II) may also be used together with so-called nitrification inhibitors and/or urease inhibitors. For this purpose the inventive compositions of the compound of formula (I) or of the mixtures of the compound of formula (I) with the compound of formula (II) may also be used in a mixture with nitrification inhibitors or in a mixture with urease inhibitors or in a mixture of nitrification inhibitors and urease inhibitors.

Fertilizer compositions that contain not only at least one compound of formula (I) or a mixture of the compound of formula (I) with the compound of formula (II) in the form of the inventive composition but also at least one further component, which is selected from urease inhibitors and nitrification inhibitors, are also subject matter of the present invention.

Suitable urease inhibitors are known to the person skilled in the art, for example from Kiss et al. (Kiss, S., Simihăian, M. 2002, *Improving Efficiency of Urea Fertilizers by Inhibition of Soil Urease Activity*, ISBN 1-4020-0493-1, Kluwer Academic Publishers, Dordrecht, The Netherlands). Suitable urease inhibitors are in particular N-alkylphosphoric acid triamide and N-alkylthiophosphoric acid triamide and mixtures thereof, as are known from WO 2009/079994 and the literature cited therein. Preferred substances are N-n-butyl-thiophosphoric acid triamide (NBPT), N-n-propylthiophosphoric acid triamide (NPPT) and mixtures thereof.

Suitable nitrification inhibitors are not only dicyandiamide but also pyrazoles and their acid addition salts, in particular their phosphoric acid addition salts, as well as 1-carboxyalkylpyrazoles and mixtures thereof. These pyrazoles and 1-carboxyalkylpyrazoles may be substituted at the carbon atoms by one or more substituents, e.g. one or two from the $C_1$-$C_4$-alkyl group, especially methyl, nitro and halogen, especially chlorine. Such compounds and their use as nitrification inhibitors are from U.S. Pat. Nos. 3,635,690, 4,969,946, EP 0808298 and EP 1120388.

Preferred nitrification inhibitors are 3-methylpyrazole compounds such as 4-chloro-3-methylpyrazole and its acid addition salts, N-hydroxymethyl-4-chloro-3-methylpyrazole and its acid addition salts, as well as 3,4-dimethylpyrazole (DMP) compounds such as 2-(3,4-dimethylpyrazol-1-yl)-succinic acid, N-hydroxymethyl-3,4-dimethylpyrazole and its acid addition salts as well as, in particular 3,4-dimethyl-pyrazole and the acid addition salts of 3,4-dimethylpyrazole, especially its phosphoric acid addition salts (DMPP).

Such fertilizer compositions contain the compound of formula (I) or a mixture of the compound of formula (I) with the compound of formula (II) and at least one further component from the group of nitrification inhibitors and urease inhibitors usually in a content of 0.001 to 5 wt %, in particular in a content of 0.002 to 3 wt % relative to the total weight of the fertilizer composition.

If such fertilizer compositions contain at least one urease inhibitor, the concentration of urease inhibitor is usually 0.001 to 3 wt %, in particular 0.002 to 2 wt % relative to the urea in the fertilizer composition.

If such fertilizer compositions contain at least one nitrification inhibitor, the concentration of nitrification inhibitor is usually 0.01 to 3 wt %, in particular 0.02 to 2 wt % relative to the total weight of the fertilizer composition, which in the case of acid addition salts of pyrazole compounds is calculated as salt.

If such fertilizer compositions contain at least one urease inhibitor and at least one nitrification inhibitor, the total concentration of nitrification inhibitor+urease inhibitor is usually 0.011 to 5 wt %, in particular 0.022 to 3 wt % relative to the total weight of the fertilizer composition. Typically the weight ratio of the at least one nitrification inhibitor to the at least one urease inhibitor is then usually 1:10 to 10:1 and preferably 1:5 to 5:1.

Fertilizer compositions that contain not only the compound of formula (I) or a mixture of the compound of formula (I) with the compound of formula (II) in the form of the inventive composition but also at least one further component selected from among urease inhibitors and nitrification inhibitors may also contain, if necessary, magnesium sulfate, preferably in the form of Epsom salts, and/or further macronutrients such as phosphorus, preferably in the form of phosphates, and/or potassium, as well as micronutrients such as manganese, zinc, copper, iron, cobalt, molybdenum and/or boron if necessary. In this case, manganese and zinc are preferably used in the form of their sulfates. Copper, cobalt and iron are preferably used in the form of chelates, for example with EDTA. Boron is preferably used as sodium borate or boric acid. Molybdenum is preferably used as sodium or ammonium molybdate or as a mixture thereof. The quantitative proportions of the compound of formula I and of the micronutrients are as stated hereinabove.

As already mentioned, solutions of the inventive compositions can be produced by dissolving the inventive compositions in a solvent, for example water. In this way the inventive compositions may be used for purposes, among others, of liquid fertilizers for fertilization by irrigation (fertigation). Water that cannot be incorporated by the roots of plant cultures, for example since it seeps into the substrate or into soil strata that cannot be reached by the roots, is known as excess water. Artificial fertigation with liquid fertilizer of the inventive composition can be carried out in such a way that essentially no excess water is produced. Preferably fertigation with liquid fertilizers of the inventive composition, in particular a mixture of liquid fertilizers of the inventive composition with other additives, for example urease inhibitors, is carried out in such a way that no excess water is produced.

The inventive composition and the inventive processes will be explained in more detail by the following examples and by FIG. 1 and FIG. 2 as well as Table 4.

The x-ray diffraction diagrams were recorded with a type D 8 Advance Diffractometer of the Bruker AXS Co. (298 K, Cu—Kα radiation: α=1.5413 Å), step width: 0.018385738, step duration: 0.2 second, detector: Lynx Eye.

The elemental analyses were performed by:

N determination DIN ISO 13878, TOC determination DIN ISO 1484, Mg/S LUFA [Agricultural Investigation and Research Institute] Association method (K+S 0905.01), H2O determination Karl-Fischer titration.

The thermogravimetric analyses were performed using a Mettler-Toledo TGA/DSC 1 thermogravimetric analyzer.

The IR analyses were performed by means of a standard FTIR spectrometer in the wavelength region of 4000 to 600 $cm^{-1}$ according to the method of attenuated total reflection (ATR).

EXAMPLE 1

1000 g (8.31 mol) ground calcined $MgSO_4$ (anhydrous, grain size <0.1 mm, produced from natural kieserite) was mixed with 499 g (8.31 mol) ground urea (grain size <1.0 mm). To this, 450 g (24.98 mol) water was added within 10 seconds under intensive stirring. Under heating to approximately 87° C., the initially liquid suspension gradually became pasty and within 5 minutes increasingly more solid, until it could no longer be mixed/stirred. After a further 12 hours of standing time (maturation) in air, a colorless solid (MgSO$_4$.CO(NH$_2$)$_2$.2H$_2$O) was obtained. The final weight was 1781 g (8.22 mol), corresponding to a yield of 99%.

EXAMPLE 2

500 g (2.13 mol) MgSO$_4$.CO(NH$_2$)$_2$.3H$_2$O was dried as a powdery sample for 24 hours at 70° C. in a laboratory drying oven. After drying, a colorless solid was obtained. The final weight was 452.35 g (2.09 mol) MgSO$_4$.CO(NH$_2$)$_2$.2H$_2$O, corresponding to a yield of 98%.

Elemental Analysis:

The theoretically and experimentally determined values of the compounds MgSO$_4$.CO(NH$_2$)$_2$.2H$_2$O and MgSO$_4$.CO(NH$_2$)$_2$.3H$_2$O are presented in the following Table 4.

TABLE 4

|  | MgSO$_4$•CO(NH$_2$)$_2$•2H$_2$O | | MgSO$_4$•CO(NH$_2$)$_2$•3H$_2$O | |
| --- | --- | --- | --- | --- |
|  | theoretical [%] | found [%] | theoretical [%] | found [%] |
| Mg | 11.2 | 11.1 | 10.4 | 10.8 |
| SO$_4^{2-}$ | 44.4 | 43.6 | 41.0 | 42.5 |
| C | 5.5 | 5.7 | 5.1 | 5.2 |
| N$_{total}$ | 12.9 | 12.8 | 11.9 | 12.2 |
| H$_2$O | 16.6 | 17.2 | 23.0 | 20.4 |

Furthermore, the biuret content of the product MgSO$_4$.CO(NH$_2$)$_2$.2H$_2$O was determined by VDLUFA [Association of Agricultural Investigation and Research Institutes] method II.1, 3.6.1. The values were typically around 0.2% for various production batches and were always below 0.9%.

Figure 2:
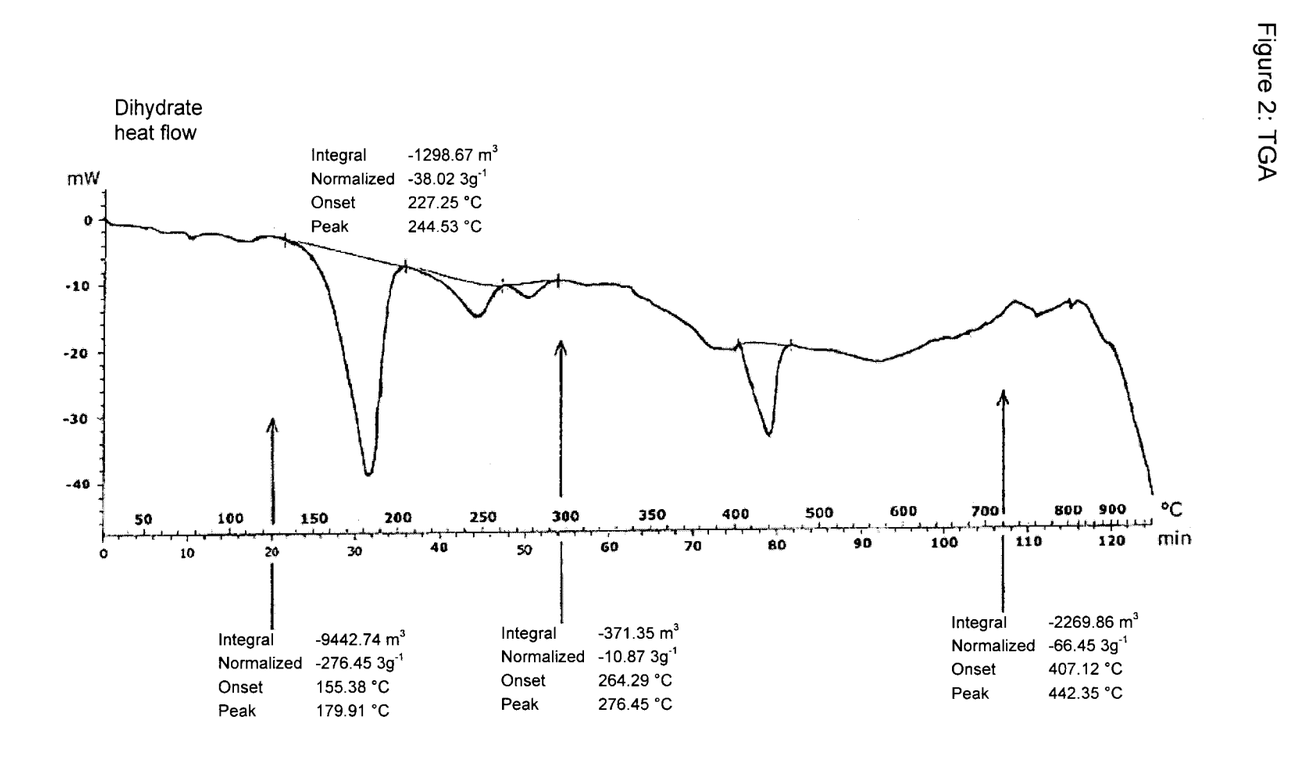
FIG. 2: Thermogravimetric diagram of the compound of formula (I).

Thermogravimetric Analysis (TGA):

In the thermogravimetric diagram (FIG. 2), MgSO$_4$.CO(NH$_2$)$_2$.2H$_2$O exhibits a weight loss of around 12% starting at a temperature of approximately 130° C. Further weight losses of 7% are observed starting at approximately 205° C. and up to 260° C. and of 3% starting at approximately 260° C. and up to approximately 290° C. At a temperature of 750° C., essentially anhydrous magnesium sulfate exists. The residual weight of experimentally around 52% (55.6% theoretical) of the starting weight is therefore in good agreement. The thermogravimetric diagram is presented in FIG. 2.

Figure 3:
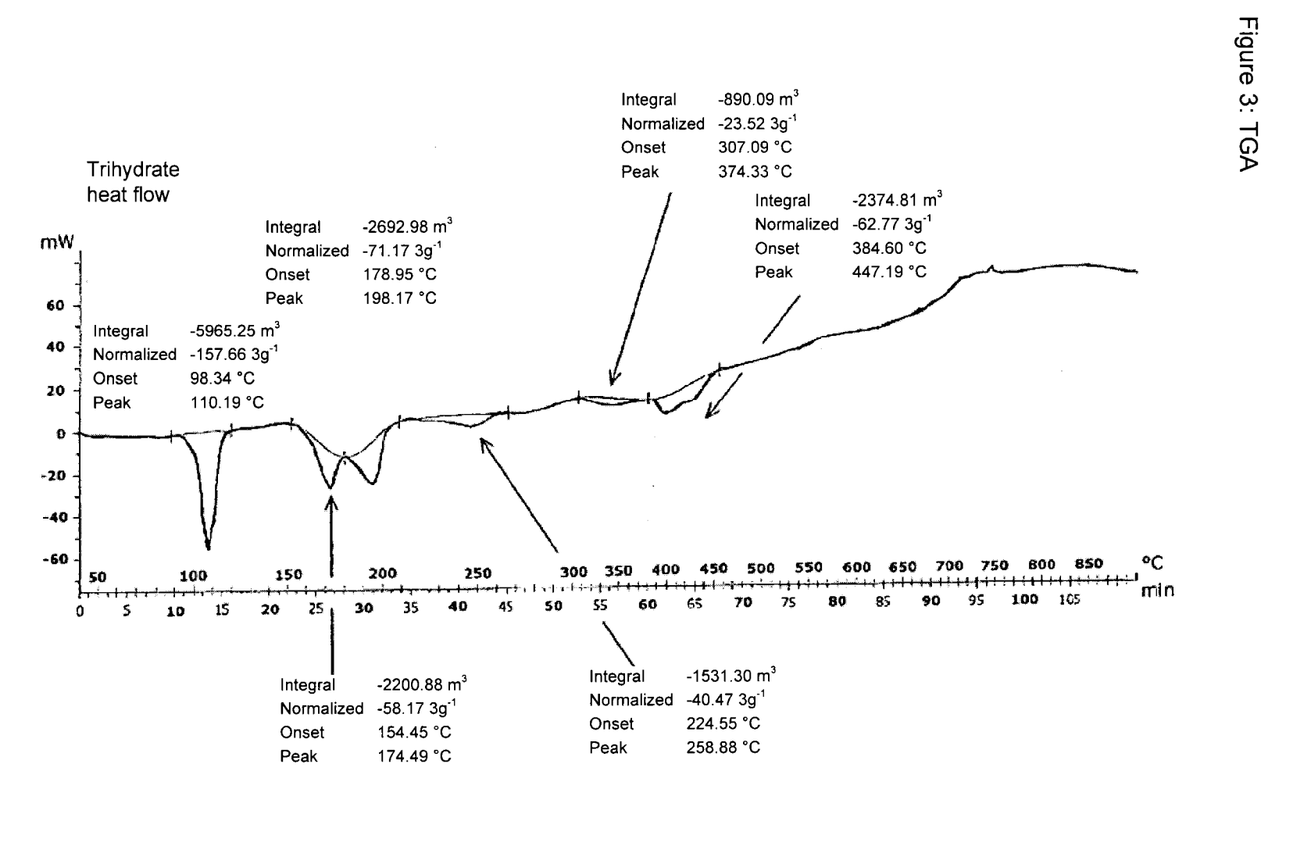
FIG. 3: Thermogravimetric diagram of the compound of formula (II).

In the thermogravimetric diagram (FIG. 3), MgSO$_4$.CO(NH$_2$)$_2$.3H$_2$O exhibits decomposition starting at a temperature of approximately 90° C., accompanied by a weight loss of approximately 6%. A further weight loss of 11% in two stages is observed starting at approximately 155° C. and up to approximately 210° C. Above 210° C., a steady weight loss is evident. At a temperature of 750° C., essentially anhydrous magnesium sulfate exists. The residual weight of experimentally around 50% (51.4% theoretical) of the starting weight is therefore in good agreement. The thermogravimetric diagram is presented in FIG. 2.

Abbreviations used (IR spectra): m=medium, st=strong, sst=very strong, sh=shoulder, br=broad.

Figure 4:
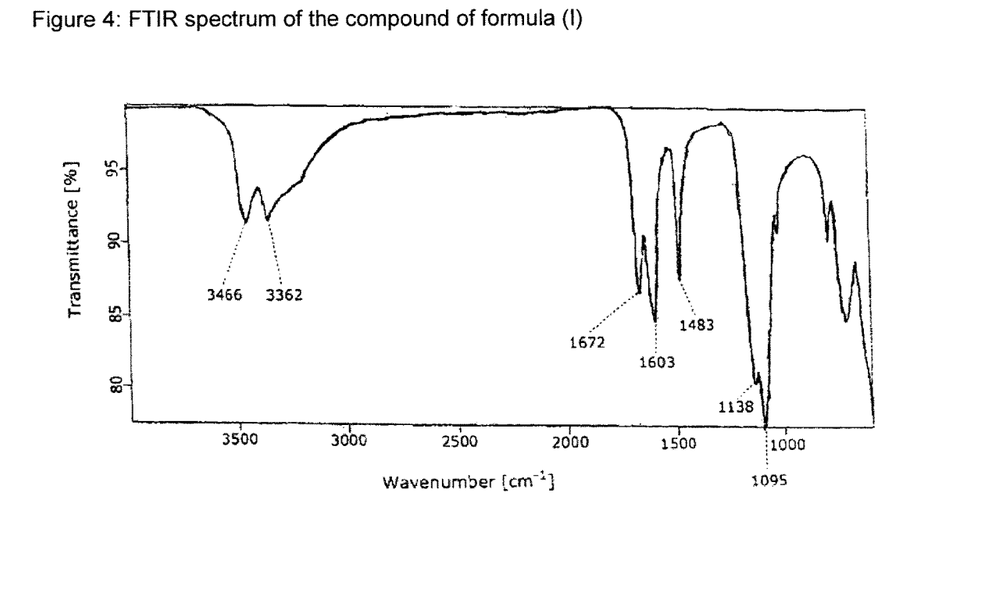
FIG. 4: FTIR spectrum of the compound of formula (I).

The IR spectrum of MgSO$_4$.CO(NH$_2$)$_2$.2H$_2$O (FIG. 4) exhibits the following bands: 3466 cm$^{-1}$ (m, br), 3362 cm$^{-1}$ (m, br, sh), 1672 cm$^{-1}$ (st), 1603 cm$^{-1}$ (st), 1483 cm$^{-1}$ (st), 1138 cm$^{-1}$ (sst), 1195 cm$^{-1}$ (sst).

Figure 5:
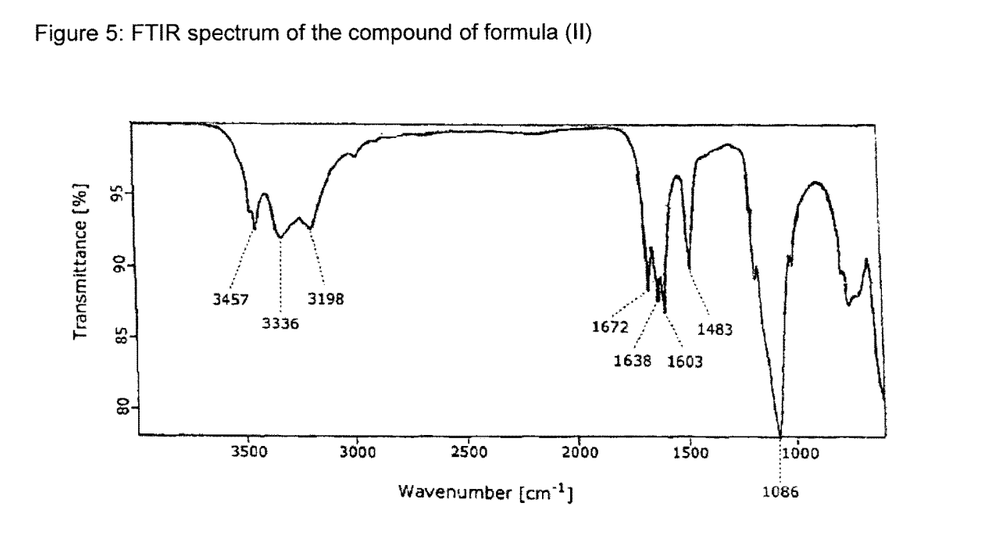
FIG. 5: FTIR spectrum of the compound of formula (II).

The IR spectrum of MgSO$_4$.CO(NH$_2$)$_2$.3H$_2$O (FIG. 5) exhibits the following bands: 3457 cm$^{-1}$ (m, sh), 3336 cm$^{-1}$ (m, br), 3198 cm$^{-1}$ (m, br), 1672 cm$^{-1}$ (st), 1638 cm$^{-1}$ (st), 1603 cm$^{-1}$ (st), 1483 cm$^{-1}$ (st), 1086 cm$^{-1}$ (sst, br).

The invention claimed is:

1. A composition, comprising:
at least 80 wt %, relative to the total weight of the composition, of a magnesium sulfate-urea compound selected from the group consisting of a compound of formula (I) and mixtures of the compound of formula (I) with a compound of formula (II):

$$[MgSO_4.mCO(NH_2)_2.nH_2O] \quad (I),$$

$$[MgSO_4.xCO(NH_2)_2.yH_2O] \quad (II),$$

wherein
m and x are in the range from 0.9 to 1.1,
n is in the range from 1.9 to 2.1 and
y is in the range from 2.9 to 3.1,
wherein the composition, relative to the total weight of the composition, comprises less than 10 wt % of free MgSO$_4$ in anhydrous form or in the form of hydrates of magnesium sulfate and less than 10 wt % of unbound urea, and
wherein the composition is a solid material and does not deliquesce after 12 hours under ambient conditions.

2. The composition according to claim 1, wherein in formula (I) the variable m has the value 1.0 and the variable n has the value 2.0, and wherein in formula (II) x has the value 1.0 and y has the value 3.0.

3. The composition according to claim 1, wherein the proportion of the compound of formula (I) relative to the total content of compounds of formulas (I) and (II) is at least 90 wt %.

4. The composition according to claim 1, wherein the proportion of the compound of formula (I) relative to the total content of compounds of formulas (I) and (II) is in the range of 20 to lower than 90 wt %.

5. The composition according to claim 1, comprising at least 90 wt %, relative to the total weight of the composition, of the magnesium sulfate-urea compound selected from the group consisting of a compound of formula (I) and mixtures of the compound of formula (I) with compound of formula (II).

6. The composition according to claim 1, wherein the composition, relative to the total weight of the composition, comprises less than 5 wt % of free MgSO$_4$ in anhydrous form or in the form of hydrates of magnesium sulfate and less than 5 wt % of unbound urea.

7. A process for production of a composition according to claim 1, said process comprising:
reacting solid anhydrous magnesium sulfate with solid urea and water at a temperature above 75° C.,
wherein anhydrous magnesium sulfate, urea and water are used in a mole ratio of magnesium sulfate to urea in the range of 1:0.9 to 1:1.1 and of magnesium sulfate to water in the range of 1:2 to 1:4.

8. The process according to claim 7, wherein the reaction is carried out in a mixing apparatus having at least one rotating mixing implement and wherein adjustment of the grain sizes is achieved during and/or directly after the reaction by increasing the speed of the mixing implements.

9. The process according to claim 7, wherein water is added to a mixture of anhydrous magnesium sulfate and urea.

10. The process according to claim 7, wherein the anhydrous magnesium sulfate is used in the form of a powder, wherein at least 95 wt % of the particles have a diameter of at most 100 μm.

11. The process according to claim 7, wherein the urea is used in the form of a powder or granules, wherein at least 95 wt % of the particles have a diameter of at most 1000 μm.

12. A process for production of a composition according to claim 1, said process comprising:

drying, at a temperature of from 65 to 95° C., a composition comprising at least 80 wt %, relative to the total weight of the composition, of the magnesium sulfate-urea compound of formula II and less than 10 wt % of free $MgSO_4$ in anhydrous form or in the form of hydrates of magnesium sulfate, and/or less than 10 wt % of unbound urea.

13. A fertilizer or an additive for a fertilizer, comprising: the composition according to claim 1.

14. A nitrogen-magnesium-sulfur fertilizer composition, comprising:
a composition according to claim 1, and
Epsom salts.

15. A fertilizer composition, comprising:
a composition according to claim 1, and
least one component selected from the group consisting of an urease inhibitor and a nitrification inhibitor.

16. A process for fertigation of a substrate used in agriculture or horticulture, said process comprising:
introducing and/or applying onto said substrate water and a composition selected from the group consisting of i) a composition according to claim 1 and ii) a composition according to claim 1 and Epsom salts; and optionally one or more further fertilizer additives;
wherein said introducing and/or applying onto said substrate proceeds in such a way that essentially no excess water is produced.

* * * * *

UNITED STATES PATENT AND TRADEMARK OFFICE
CERTIFICATE OF CORRECTION

Page 1 of 1

PATENT NO.        : 9,994,491 B2
APPLICATION NO.   : 14/653668
DATED             : June 12, 2018
INVENTOR(S)       : Armin Dietrich et al.

It is certified that error appears in the above-identified patent and that said Letters Patent is hereby corrected as shown below:

On the Title Page

Item (72), in the listing of the inventors, the city of inventor Armin DIETRICH is currently:
"Weissenbom"
And should be:
--Weissenborn--

Signed and Sealed this
Fifth Day of February, 2019

Andrei Iancu
*Director of the United States Patent and Trademark Office*